(12) United States Patent
Lacza et al.

(10) Patent No.: US 8,404,266 B2
(45) Date of Patent: Mar. 26, 2013

(54) METHOD FOR STABILIZATION OF S-NITROSOGLUTATHIONE AND COMPOSITION PREPARED BY THE SAME

(75) Inventors: Zsombor Lacza, Budapest (HU); István Hornyák, Miskolc (HU)

(73) Assignee: Pharmagenix AG, Zürich (CH)

( * ) Notice: Subject to any disclaimer, the term of this patent is extended or adjusted under 35 U.S.C. 154(b) by 189 days.

(21) Appl. No.: 12/863,816

(22) PCT Filed: Jan. 16, 2009

(86) PCT No.: PCT/HU2009/000004
§ 371 (c)(1),
(2), (4) Date: Dec. 6, 2010

(87) PCT Pub. No.: WO2009/090439
PCT Pub. Date: Jul. 23, 2009

(65) Prior Publication Data
US 2011/0136910 A1    Jun. 9, 2011

(30) Foreign Application Priority Data

Jan. 16, 2008   (HU) ..................................... 0800031

(51) Int. Cl.
*A61K 9/00*    (2006.01)
*A61K 38/06*    (2006.01)

(52) U.S. Cl. ........ 424/425; 424/485; 424/486; 424/488; 514/21.9

(58) Field of Classification Search .................. None
See application file for complete search history.

(56) References Cited

U.S. PATENT DOCUMENTS

2002/0002136 A1    1/2002  Hebert
2007/0185205 A1*   8/2007  Hunt et al. .................... 514/565

FOREIGN PATENT DOCUMENTS

WO    WO 2007064895 A2 *  6/2007

OTHER PUBLICATIONS

Zhelyaskov et al.; Control of NO Concentration in Solutions of Nitrosothiol Compounds by Light; Photochemistry and Photobiolgy; 1998; vol. 67(3), pp. 282-288.

Smith et al.; Kinetics and Mechanism of the Decomposition of S-Nitrosoglutathione by L-Ascorbic Acid and Copper Ions in Aqueous Solution to Produce Nitric Oxide; Nitric Oxide; 2000; vol. 4, No. 1, pp. 57-66.

Cantoni et al.; Stability of Nitroso Derivatives (Nitrosothiols, Nitrosophenols, and Nitrosohemoglobin) at Alkaline pH; Industrie Alimentari; Jan. 1975; vol. 14, No. 7-8, pp. 79-81.

Seabra et al.; Solid Films of Blended Poly(Vinyl Alcohol)/Poly(Vinyl Pyrrolidone) for Topical S-Nitrosoglutathione and Nitric Oxide Release; Journal of Pharmaceutical Sciences; May 2005; vol. 94, No. 5, pp. 994-1003.

Khan et al.; S-Nitrosoglutathione reduces inflammation and protects brain against focal cerebral ischemia in a rat model of experimental stroke; Journal of Cerebral Blood Flow & Metabolism; Jan. 2005; vol. 25, pp. 177-192.

Kuo et al.; Nitrosoglutathione Modulation of Platelet Activation and Nitric Oxide Synthase Expression in Promotion of Flap Survival after Ischemia/Reperfusion Injury; Journal of Surgical Research; 2004; vol. 119, pp. 92-99.

Seabra et al.; Polynitrosated Polyesters: Preparation, Characterization, and Potential Use for Topical Nitric Oxide Release; Biomacromolecules; 2005; vol. 6, pp. 2512-2520.

Seabra et al.; Poly(vinyl alcohol) and poly(vinyl pyrrolidone) blended films for local nitric oxide release; Biomaterials; 2004; vol. 25, pp. 3773-3782.

Seabra et al.; Topically applied S-nitrosothiol-containing hydrogels as experimental and pharmacological nitric oxide donors in human skin; British Journal of Dermatology; 2004; vol. 151, pp. 977-983.

Seabra et al.; S-Nitrosoglutathione incorporated in poly(ethylene glycol) matrix: potential us for topical nitric oxide delivery; Nitric Oxide; 2004; vol. 11, pp. 263-272.

Sogo et al.; S-Nitrosothiols cause prolonged, nitric oxide-mediated relaxation in human saphenous vein and internal mammary artery: therapeutic potential in bypass surgery; British Journal of Pharmacology; 2000; vol. 131, pp. 1236-1244.

Sogo et al.; Inhibition of Human Platelet Aggregation by Nitric Oxide Donor Drugs: Relative Contribution of cGMP-Independent Mechanisms; Biochemical and Biophysical Research Communications; 2000; vol. 279, pp. 412-419.

\* cited by examiner

*Primary Examiner* — Jeffrey E Russel
(74) *Attorney, Agent, or Firm* — Jason D. Voight

(57) ABSTRACT

The invention relates to pharmaceutical compositions having alkaline pH comprising S-nitrosoglutathione (GSNO) as active ingredient together with usual additives, optionally with one or more polysaccharide-type polymer(s). Another subject of the invention is a method for stabilizing a solution or non-solid composition containing GSNO wherein the pH of the solution or composition is adjusted to an alkaline value.

16 Claims, 3 Drawing Sheets

US 8,404,266 B2

METHOD FOR STABILIZATION OF S-NITROSOGLUTATHIONE AND COMPOSITION PREPARED BY THE SAME

This is the National Phase of PCT/HU2009/000004, filed Jan. 16, 2009.

FIELD OF THE INVENTION

The invention primarily relates to pharmaceutical compositions having alkaline pH comprising S-nitrosoglutathione (GSNO) as active ingredient together with usual additives, optionally with one or more polysaccharide-type polymer(s). The invention is based on the unexpected discovery that GSNO produced in good yield under acidic condition is more stabile under alkaline condition, especially in the presence of stabilizing polymers.

STATE OF THE ART

Vasoconstriction that develops during microcirculatory disturbances increasing susceptibility to thrombosis and accumulation of free radicals having released in certain metabolic problems cause complex tissue damage that leads to a decrease in wound healing potential and to chronic ulceration in several cases [Greenman et al., 2005, Lancet, 366, 1711-7; Sigaudo-Roussel et al., 2004, Diabetes, 53, 1564-9; Veves et al., 1998, Diabetes, 47, 457-63; Hile and Veves, 2003, Curr. Diab. Rep., 3, 446-51; Nikolovska et al., 2005, Acta Dermatovenerol Croat, 13, 242-6]. Numerous dermatological medicaments are available for treating microcirculatory disturbances developing in, e.g., diabetes or vasoconstriction. Characteristically, these compositions contain essential oils (e.g. rosemary) and other non specific active ingredients having clinically unverified efficiency. According to experimental results, nitric oxide (NO) can beneficially affect the microcirculatory disturbance [Cals-Grierson and Ormerod, 2004, Nitric Oxide, 10, 179-93]. NO is a quickly reacting gaseous compound, having—among others—smooth muscle relaxing effect, which is used as an inhalant in physiotherapy. Due to its consistency, NO can hardly be used for dermatological purposes, however, clinical observation confirms its effectiveness for treating non-healing ulcers [Miller et al., 2004, J. Cutan. Med. Surg., 8, 233-8]. Alternatively, by using NO donor compounds, such as sodium nitroprusside, therapeutically effective amounts of NO can be transferred to the epidermis. However, the administration of these compounds is accompanied by several new problems that make their application difficult. Namely, most of the NO donors release not only NO but also other reactive nitrogen species which can be harmful for the tissues during long term application. A more important problem comes from the fact that the degradation of NO donors is very fast, accordingly blood-stream increasing compositions having suitable stability and predictable local vasodilator effect are not optimal. Third, by absorbing through the skin, the slowly degrading NO donor compositions such as nitroglycerine reach the systemic circulation and exert their effect in tissues far from the treated area, which is not preferable. Nitrate-containing skin patches are widely used in medicine, and their effects are partly based on their NO-donor feature. However, the nitrate considered as a precursor of the vasodilator agent (NO) is transferred to the systemic circulation without the increase in blood circulation of the directly exposed skin surface. The desired effect of a NO-donor for treating microcirculatory disturbance is just the opposite: it should generate local vasodilation without exerting significant systemic effects.

Certain scientific studies have already been directed to using the substrate of NO synthase, i.e. L-arginine, in the treatment of microcirculatory disturbances [Fossel, 2004, Diabetes Care, 27, 284-5]. The NO synthase system itself is necessary for the L-arginine to exert its activity, however, the damage of this enzyme system is characteristic for the microcirculatory disturbance. Additionally, the L-arginine is also a substrate of different other NO-synthase-competing enzymes, such as argininase, arginine decarboxylase etc. Thus, on the basis of the above, obviously it is more preferable to administer the NO to the local circulatory system, than the application of its precursor.

Numerous patents are known where NO-donor compound is used in topical compositions releasing nitrogen monoxide in a desired speed. For example, the U.S. Pat. No. 6,287,601 B1 discloses a formulation in which nitroglycerine, hydroxilamine, nitroprusside, nitrate or azide are used as NO-donor compounds in combination with a non-steroidal anti-inflammatory drug (NSAID). The U.S. Pat. No. 5,519,020 discloses the use of a water-insoluble nitrogen oxide/polymer adduct, where the polymer might be, e.g., polyethyleneimine cellulose. The U.S. Pat. No. 7,048,951 B1 B2 discloses that powdered sodium nitrite, ascorbic acid and preferably maleic acid are mixed, and the obtained mixture releases nitrogen monoxide when exposed to water.

Several embodiments are known where a polymer-based matrix comprises nitrogen, monoxide bound physically or chemically. The U.S. Pat. No. 5,994,444 discloses that a biologically degradable polymer (preferably poly-L-lactic acid) is impregnated with nitrogen oxid donor compound, preferably with an inorganic nitrite compound. The U.S. Pat. No. 5,770,645 2 discloses polymers which are derivatized with —NOx group which is then able to release NO.

The NOlabs (Helsinborg, Sweden) submitted several applications (WO2006/084911-14) where nitrogen monoxide is used for the treatment of different diseases, including diabetic ulcer and neuropathy. In these diseases NO releasing polymers are used to obtain the desired NO release. Preferably, an NO-derivative of linear polyethyleneimine (L-PEI-NO) is used. In the general disclosure the chitosan is referred to as a type of certain polymers that can be derivatized with NO. Furthermore, the polysaccharides are referred to only as an inert support for the NO-releasing polymers (e.g. WO 2006/084912, pp. 11-12).

Research studies verify that an endogenous nitrosothiol compound, the GSNO, which is a natural NO-donor, is particularly suitable for the preparation of local vasodilator composition [Sogo et al., 2000, Br. J. Pharmacol., 131, 1236-44]. NO and reduced glutathione with known antioxidant effects are generated during the decomposition of GSNO. Due to its vasodilatory and platelet aggregation inhibitory effects, the NO penetrated into the local circulation improves blood circulation in the skin and inhibits thrombosis formation [Khan et al., 2005, J. Cereb. Blood Flow Metab., 25, 177-92; Kuo et al., 2004, J. Surg. Res., 119, 92-9; Sogo et al., 2000, Biochem. Biophys. Res. Commun., 279, 412-9]. However, its applicability is limited since in aqueous solutions the half-life of this compound is very short, only 5.5 hours.

The stability of GSNO could be significantly improved by using pharmaceutically known vehicles. Poly(ethyleneglycol), poly(vinyl-pyrrolidone), or poly(vinyl-alcohol) are all suitable to decrease the degradation rate of GSNO, primarily by forming hydrogen bridges [A. B. Seabra et al., May 2005, J. Pharm. Sci., 95, No. 5, 994-1003; A. B. Seabra, M. G de Oliveira, 2004, Biomaterials, 25, 3773-82; Seabra et al., 2004, Nitric Oxide, 11, 263-72]. However, these approaches are not sufficient to generate stabile composition appropriate for everyday medical practice, since the half-life of the agent at ambient temperature or at 4° C. could be extended only for a few days.

The role of stabilizing hydrogen bridges is also emphasized in the U.S. Pat. No. 7,015,347 B2 patent, where compounds having intramolecular OH or SH groups capable of stabilizing the S—NO group were claimed.

Additionally, NO-donor macromolecules containing S—NO groups covalently bound to polyethylene glycol framework are also known [Seabra et al., 2005 September-October, Biomacromolecules, 6(5), 2512-20].

On the basis of our research it can be stated that certain polysaccharides (preferably the chitosan and similar natural polymers) are capable of stabilizing GSNO. It is supposed they can do so through the interaction of the hydroxil groups of the macromolecules.

Only one publication discloses that GSNO comprising hydrogels were administered to healthy volunteers and NO-dependent increase in local blood-stream was observed in the study [Seabra et al., 2004, Bristish J. Dermatol, 151, 977-83]. The rate of vasodilation correlated well with both the applied concentration of GSNO and the metabolic NO-products measured in the skin, thus verifying the specificity of the effect. No side effects were reported by the subjects during the study. In the study poly(ethyleneoxide)/poly(propyleneoxide) based Synperonic F127 hydrogels (Uniquema, Belgium) were used as vehicles. However, hydrogel composition used in the study is not suitable for clinical application, since it does not decelerate the decomposition of GSNO, hence it should be prepared freshly for each administration.

Nitrosoglutathione derivatives developed for local vasodilation are also known [see Lacer S A, Hungarian patent application No. P0105203]. These cyclic compounds have not been applied in the clinical practice so far, this is why there is no information about their efficiency or metabolism. Generally speaking, the endogenous agent with well-known metabolism, such as GSNO, has probably less side effects compared with synthetic derivatives, therefore it is more preferable.

The object of the invention is the enhancement of the stability of GSNO and consequently the development of a vasodilator composition suitable for dermatological application which is sufficiently stable under storage conditions in the field of pharmacy as well as in households. Due to its GSNO content the composition of the invention is capable of causing clinically significant increase in blood-flow, therefore, it can preferably be used for the treatment and the prevention of ulcer, neuropathy, such as diabetic peripheral neuropathy, and diabetic foot syndrome.

SUMMARY OF THE INVENTION

In searching for the solution to the problems set forth above, the inventors conducted extensive studies and discovered that the metabolic rate of GSNO can significantly be decreased under alkaline conditions. This experimental result is also unexpected since GSNO is produced under acidic conditions to obtain a maximum yield (see the description of GSNO below and FIG. 1).

Unexpectedly, it was found that the stability of GSNO has a plateau-like maximum within the pH range of about 7.5 to 10, where the pH range of about 8 to 9 is preferable, in which case the molecule has a more stable configuration. Additionally, we also discovered that GSNO shows buffering capacity within this range (see FIG. 2).

In a preferable embodiment of the invention very good stability is observed at pH value of about 8.6 compared with e.g. the conventionally applied pH 4.26 (see FIG. 3). It should be noted that at pH value of about 4.26 the GSNO behaves also as a buffer, thus, until now, subsequently to the conventional acidic preparation, GSNO has been stored in a solution having approximately the above pH.

Interestingly, GSNO metabolism gets accelerated when conditions become more alkaline (see the curve of pH 12).

Based on the above experimental results, the invention provides primarily a composition comprising an alkaline GSNO (preferably having a pH value of 7 to about 10) which remains suitably stable during storage, after being placed on the skin (alternatively, after a neutralization preceeding the application) the composition exerts significant local vasodilative and blood-stream increasing effects, thus it can be used in the prevention and treatment of the above mentioned diseases.

The inventors also discovered that an especially stable composition can be obtained when one or more suitable polymer(s) is(are) also used in the composition. It was found that the stabilizing effect of polymers (e.g. PVA, PEG) capable of stabilizing GSNO can significantly be enhanced when the pH value of the composition is within the alkaline range. Preferably, in the application of chitosan (which is a natural acidic polymer) the composition is alkalified preferably to a pH value of around 7 (i.e. to an about natural or slightly alkaline value).

Accordingly, the present invention relates to the following subject matters:

1. Pharmaceutical composition comprising GSNO as active ingredient together with usual additives, optionally with one or more pharmaceutically acceptable polymers(s) characterized in that the pH value of the composition is higher than 7, preferably around 7.5-10, more preferably around 8-9.

2. Pharmaceutical composition according to item 1 characterized in that the composition contains one or more other pharmaceutically acceptable polymers selected from the following group: polysaccharides, PVA, PVP, PEG, alginic acid and its salts and esters.

3. Pharmaceutical composition according to item 2 characterized in that the composition is an aqueous gel and contains PVA and PEG polymers as pharmaceutically acceptable polymer, optionally together with a polysaccharide, preferably together with chitosan.

4. Pharmaceutical composition in a solid form characterized in that it is prepared by drying, preferably by lyophilizing of the composition according to any of the items 1 to 3.

5. Method of stabilizing a solution or non-solid composition containing GSNO characterized in that the pH of the solution or composition is adjusted to a value higher than 7, preferably to about 7.5-10, more preferably to about 8-9.

6. Method of item 5 characterized in that the solution is aqueous.

7. Method of item 5 characterized in that the composition is a non-solid pharmaceutical composition containing one or more pharmaceutically acceptable polymer(s) and additive(s).

8. Method of item 7 characterized in that the composition contains one or more other pharmaceutically acceptable polymers selected from: polysaccharides, PVA, PVP, PEG, alginic acid and its salts and esters.

9. Method of item 8 characterized in that the composition is an aqueous gel and contains PVA and PEG polymers as pharmaceutically acceptable polymer, optionally together with a polysaccharide, preferably together with chitosan.

DETAILED DESCRIPTION OF THE INVENTION

Definitions

GSNO

The GSNO (S-nitrosoglutathione) is an endogenous compound having an important role in the metabolism of NO. The reduced glutathione as a free radical capturing tripeptide found in cells and certain cell components, such as mitochondria, is capable of reacting with NO which binds to the sulphur atom of the side-chain of the central tyrosine in the molecule and a nitrosoglutathione is formed. During the metabolism of GSNO this bond dissociates and the NO is released, thus the GSNO is not only a free radical capturing molecule but it is also an NO transporter molecule. A significant amount of GSNO can be found not only in the cells, but it is also present in the extracellular space, e.g. in the blood, thus its physiological function is the contribution in NO transport and in maintenance of constant NO blood level.

Several reaction schemes are known for synthesizing GSNO. According to a known reaction, sodium nitrite and later acetone is added to cold, acidic aqueous glutathione solutions, preferably in multiple aliquots and during agitation. After the separation and the washing of the resulting precipitate, suitably pure S-nitrosoglutathione is obtained [Tetrahedron Letters, Vol. 26, No. 16, 2013-2016, 1985]. Other preparation methods are disclosed in Acc. Chem. Res. 1999, 32, 869-876; J. Chem. Soc. Perkin Trans. I., 1994, where the feasibility of conducting the reaction in acidic environment is also disclosed.

The GSNO is a brown colored compound having a characteristic absorption spectrum. One of its two characteristic peaks is in the UV range, while the maximum of the other is around 540 nm. During decomposition the absorption spectrum of GSNO goes through a change. The change in the height of the peak at 540 nm is linearly proportional with the concentration of GSNO. Wavelengths at far IR range can be used as background absorption, since no change occurs in them during the decomposition process of GSNO. These features allow monitoring the concentration of GSNO spectrophotometrically.

Pharmaceutically Acceptable Polymers

The composition may contain one or more pharmaceutically acceptable polymer-like compound(s) such as poly(vinylalcohol) [PVA], polyethyleneglycol [PEG], poly(vinylpyrrolidone) [PVP], acrylic acid based polymer (e.g. polyacrylic acid polymer commercialized as "carbomer"), cellulose, alginic acid and its salts and esters (e.g., alginate-based polymer).

The term "polysaccharide" means macromolecular carbohydrates where the monomers are bound to each other through glycoside bounds (glycans). It includes important biopolymers, such as the starch, glycogen and cellulose (considered as polycondensation products of dextran and glucose), the inulin (the polycondensation product of fructose), chitin, alginic acid etc. Since the polysaccharides mentioned above are polycondensation products of a specific saccharide they might be considered as homopolymers. Certainly, polysaccharides comprising different monomers (heteroglycans, such as hemicelluloses, heparin, hyaluric acid, murein) can also be used in the embodiment of the invention. Several known derivatized (e.g. deacyled, sulfonated, etc.) polysaccharides can also be used in the embodiment of the invention. Polysaccharides used in the invention are preferably stable under alkaline conditions (such as alginic acid, its salts and esters). However, polysaccharides having the highest stability under slightly acidic pH conditions but also having sufficient stability in neutral or alkaline conditions can also be used, such as chitosan [β-1,4-poly-D-glucosamine which can be considered as a deacylated derivative of chitin (β-1,4-poly-N-acetyl-D-glucosamine)].

Pharmaceutically Acceptable Additives

Furthermore, the composition may contain any such usual additive that is necessary for the optimalization of the physical features of the composition. Thus, it may contain inert vehicles, gelating agents, viscosity enhancers, colourants, buffering agents, odorants, preservatives, stabilizers etc.

The compositions according to the invention are preferably hydrogels or such dry compositions that can be transformed to hydrogel for use in medication by contacting them with water.

The hydrogel-type composition preferably contains distilled water or aqueous solution.

Method for Preparation of the Composition

The compositions of the invention are prepared by a method known per se. Preferably, an aqueous gel is prepared from one ore more suitable polymer(s) (preferably, PAG, PVA, alginate, polysaccharide), then the GSNO in a desired concentration is mixed into it.

Optionally, the obtained alkaline gel is lyophilised. For a long-time storage, it is feasible to keep the lyophilised composition in a refrigerator. Feasibly, the lyophilised composition is regenerated with water, preferably with distilled water, preferably under alkaline conditions, right before the application.

Adjusting the pH

The adjustment of pH of the composition can be performed by:

a) adjusting the pH value after admixing the components;

b) adjusting the pH value of the initial GSNO solution to the level desired, then the pH value is checked after the addition of further components and, if necessary, adjusted to the desired value by the addition of alkali or acid.

Alkalifying or acidifying can be carried out by using pharmaceutically accepted alkalis (such as, hydroxides of alkaline metals or alkaline earth metals, e.g. sodium hydroxide) or pharmaceutically accepted acids (such as hydrogen halogenides, e.g. hydrogen chloride, common organic acids, e.g. lactic acid etc.). PH values are measured as usual (using pH metering electrodes, titration etc.).

Symbols Indicate the Following pH Values:

*: pH=0.3;
♦: pH=4.26;
□: pH=7.4;
■: pH=8.6;
○: pH=12.6.

Figure 1:
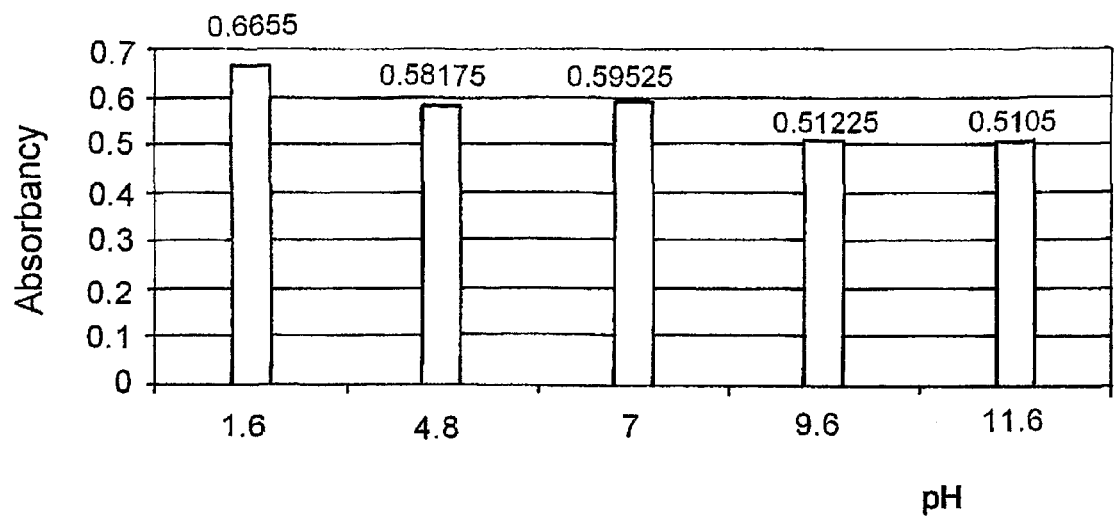
FIG. 1 shows the GSNO production at different pH values. Absorbance values measured are proportional with GSNO concentrations obtained. On the X-axis the pH values and on the Y-axis the absorbency values are given.
Figure 4:
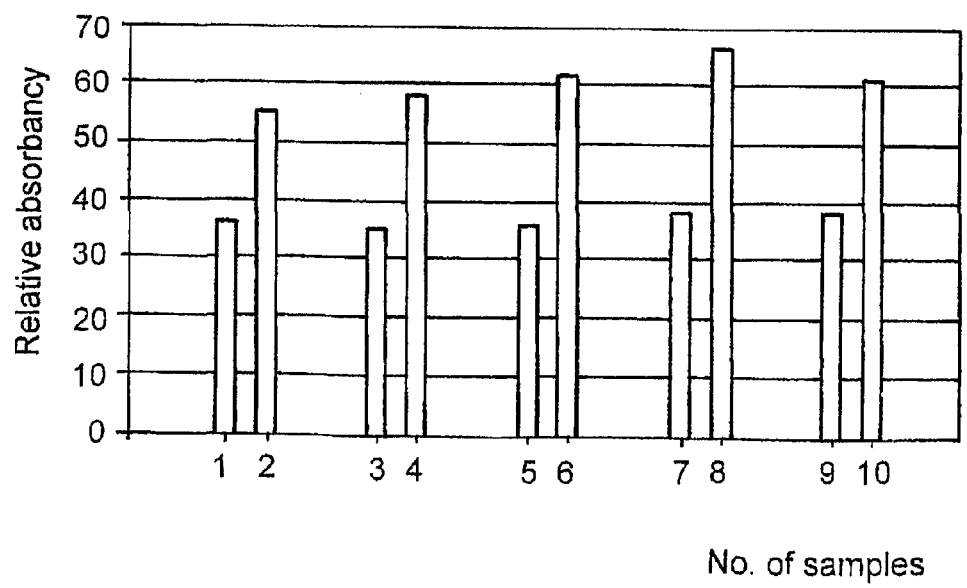
Figure 2:
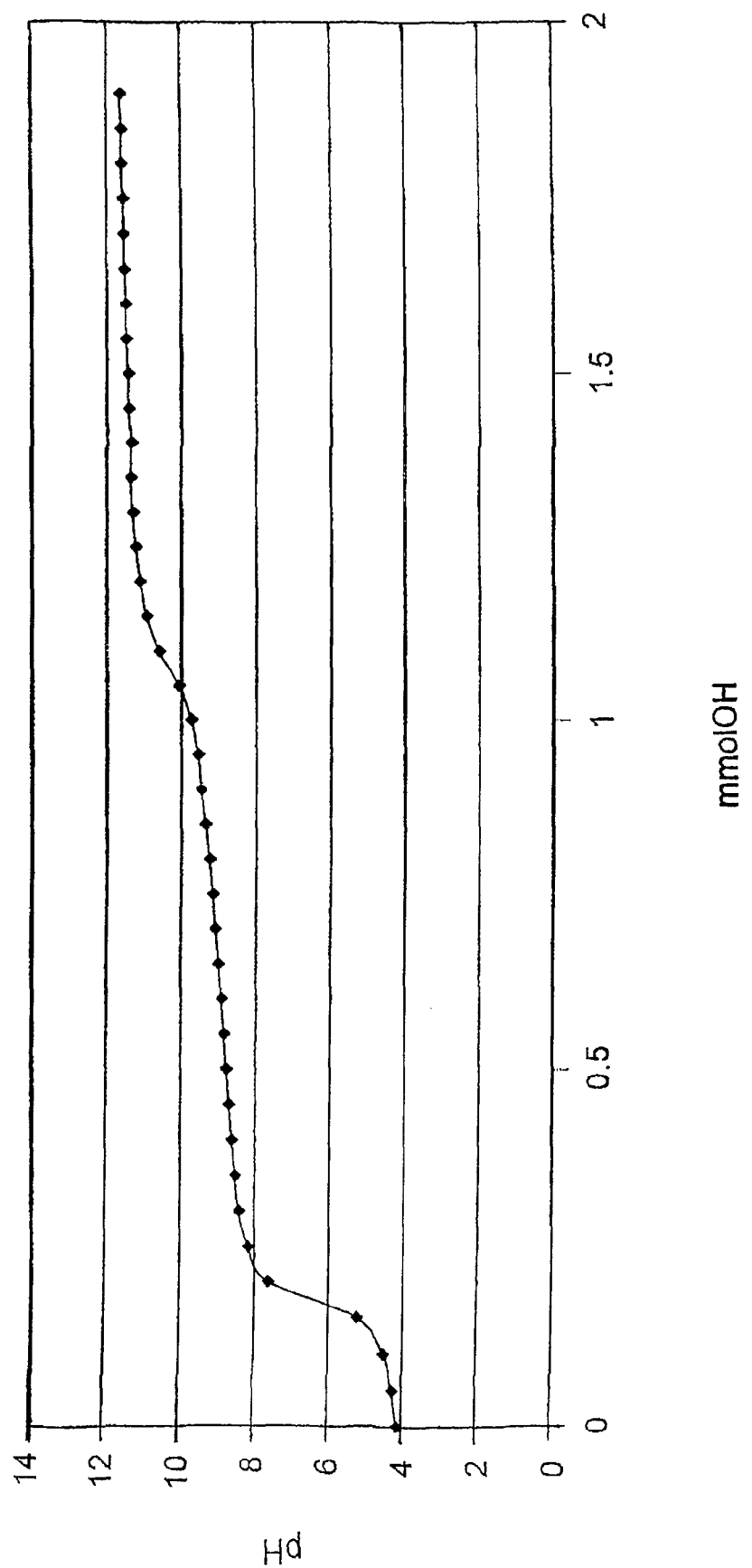
FIG. 2 shows the curve of alkaline titration (performed with NaOH) of GSNO. It can be seen that buffering capacity is exerted at pH 8-10.

FIG. 4 shows the results of measurements performed according to example 3. On the X-axis the number of the solution and on the Y-axis the relative absorbency values are given (the absorbency of the starting solution is regarded as 100). Decomposition of each solution was observed on day 36.

EXAMPLES

The list of materials used in the examples are as follows:
1. Chitosan, technical purity (Sigma-Aldrich)
2. Chitosan, low molecular weight (Sigma-Aldrich)
3. Chitosan, medium molecular weight (Sigma-Aldrich)
4. L-glutathione (reduced, 99% purity, Sigma-Aldrich)
5. Sodium nitrite (99% purity, Sigma, Aldrich)
6. Polyethyleneglycol (average mol wt: 200; Sigma-Aldrich)
7. Poly(vinyl alcohol), 80% hydrolyzed, average mol wt: 9000-10000 (Sigma-Aldrich)
8. Lactic acid (Fluka)
9. Analytically pure deionized water (Millipore Milli-Q)

Measuring GNSO

The decomposition of GSNO was monitored spectrophotometrically, since the absorption spectrum of GSNO undergoes changes and the size change of the peak at 540 nm is linearly proportional with the concentration of GSNO. Wavelengths at far IR range were used as background absorption, since no change occurs in them during the decomposition of GSNO.

1. Example 1

Preparation of GSNO
Method A
1.53 g (5 mmol) L-glutathione (GSH) was dissolved in a mixture of 5.5 ml water and 2.5 ml (2 N) aqueous HCl solution cooled in ice bath, then 0.345 g (mmol) sodium nitrite was added. The mixture was stirred for 40 min at 5° C., then 10 ml acetone was added and the solution was stirred for further 10 min. The precipitated brown deposit was filtered and subsequently washed with ice-cold water (5×1 ml), acetone (3×10 ml) and ether (3×10 ml). Thus 1.29 g (3.8 mmol) of S-nitrosoglutathione was obtained (76% yield).

Method B
First 0.204 g (0.666 mmol) GSH, then equimolar amount of $NaNO_2$ was added to 8 ml deionized water, and the mixture was kept on ice and stirred for further 10 min in dark. The calculated concentration of the obtained fresh solution is 2.726 w %.

In subsequent experiments freshly prepared GSNO solution according to above method B was used.

Example 2

General Preparation Method of Solutions Studied
Previously prepared PVA and chitosan gels were mixed to the GSNO solution of example 1B in an amount diluting the original GSNO solution to 3-fold. 200 μl aliquots were pipetted into the wells of a 96-well plate in duplicates. The plates were covered and stored at 4° C. in dark. Since during storage the preparations lost different amounts of water, after finishing the experiment it became necessary to complete them with water to the original volume. GSNO concentration was expressed as the % decrease of optical density measured spectrophotometrically at the start and at the end of the experiment.

3. Example 3

36-Day Stability Data
The experiments were performed analogously to the way described in example 2 by using the following gels. Measurements were performed after 36 days.

1-2. Solutions 1-12:
Stock solution: 0.2 g PVA and 0.6 g PEG dissolved in 4 ml of water (Millipore Milli-Q). The following solutions were made from the stock:
1. solution 1: 800 μl stock solution, pH 5.
2. solution 2: 800 μL stock solution having a pH value adjusted to 9 with NaOH.

3-4. Solution 3-4:
Stock solution: 0.15 g PVA and 0.65 g PEG dissolved in 4 ml of water (Millipore Milli-Q).
3. solution 3: 800 μl stock solution, pH 5.
4. solution 4: 800 μl stock solution having a pH value adjusted to 9 with NaOH.

5-6. Solutions 5-6:
Stock solution: 0.1 g PVA and 0.7 g PEG dissolved in 4 ml of water (Millipore Milli-Q).
5. solution 5: μ800 μl stock solution, pH 5.
6. solution 6: 800 μl stock solution having a pH value adjusted to 9 with NaOH.

7-8. Solutions 7-8:
Stock solution: 0.05 g PVA and 0.75 g PEG dissolved in 4 ml of water (Millipore Milli-Q).
7. solution 7: 800 μ800 μl stock solution, pH 5.
8. solution 8: 800 μl stock solution having a pH value adjusted to 9 with NaOH.

9-10. Solutions 9-10:
Stock solution: 0.8 g PEG dissolved in 4 ml of water (Millipore Milli-Q) (PVA-free solution).
9. solution 9: μ800 μl stock solution, pH 5.
10. solution 10: 800 μl A stock solution having a pH value adjusted to 9 with NaOH.

FIG. 4 shows the results obtained. It is clear that after 36 days the decomposition of GSNO is significantly lower in the alkaline polymeric solutions.

Figure 3:
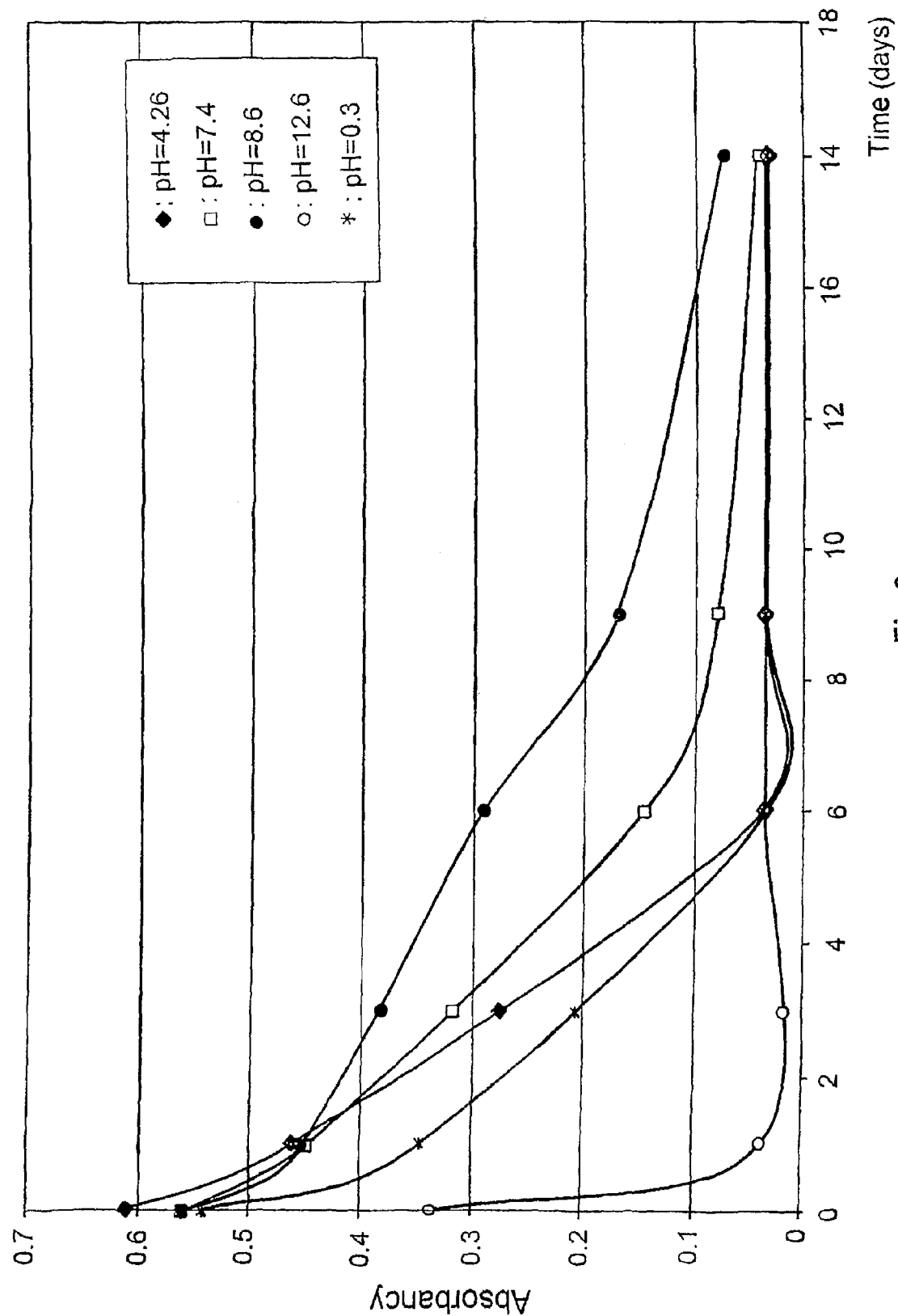
FIG. 3 shows the results of GSNO metabolism obtained at different pH values. On the X-axis the time (given in days) and on the Y-axis absorbency values are given.

The comparison of FIGS. 3 and 4 also shows that the stability enhancement of GSNO found in alkaline conditions can be further increased by using polymers with stabilizing effect. The polymers in themselves enhance the stability of GSNO since even at day 36 a relative absorbance value of around 30 is observed with acidic solutions containing the polymer. Surprisingly, stabilizing effect of the polymers can be significantly enhanced when the polymers are used under alkaline conditions—with solutions 6 and 8 the relative absorbance values are higher then 60, i.e. about 80% increase in effect is found.

The invention claimed is:

1. A pharmaceutical composition comprising GSNO as active ingredient together with one or more pharmaceutically acceptable additive(s), and with one or more pharmaceutically acceptable polymers(s) selected from the group consisting of polysaccharides, PVA, PVP, PEG, alginic acid and salts and esters of alginic acid, characterized in that the pH value of the composition is higher than 7.

2. The pharmaceutical composition according to claim 1 characterized in that the composition is an aqueous gel and contains PVA and PEG polymers as pharmaceutically acceptable polymers, optionally together with a polysaccharide.

3. A pharmaceutical composition in a solid form characterized in that it is prepared by drying the composition according to claim 1.

4. A method for stabilizing a solution or non-solid composition containing GSNO characterized in that the pH of the solution or non-solid composition is adjusted to a value higher than 7 and the solution or non-solid composition contains one or more pharmaceutically acceptable polymers selected from the group consisting of polysaccharides, PVA, PVP, PEG, alginic acid and salts and esters of alginic acid.

5. The method of claim 4 characterized in that the solution is aqueous.

6. The method of claim 4 characterized in that the non-solid composition is a non-solid pharmaceutical composition containing one or more pharmaceutically acceptable polymer(s) and one or more pharmaceutically acceptable additive(s).

7. The method of claim 4 characterized in that the non-solid composition is an aqueous gel and contains PVA and PEG polymers as pharmaceutically acceptable polymers, optionally together with a polysaccharide.

8. The pharmaceutical composition according to claim 1 characterized in that the pharmaceutically acceptable additive(s) is/are selected from the group consisting of inert vehicles, gelating agents, viscosity enhancers, colorants, buffering agents, odorants, preservatives and stabilizers.

9. The pharmaceutical composition according to claim 1 characterized in that pH value of the composition is around 7.5-10.

10. The pharmaceutical composition according to claim 1 characterized in that pH value of the composition is around 8-9.

11. The pharmaceutical composition according to claim 1 characterized in that the composition is an aqueous gel and contains PVA and PEG polymers as pharmaceutically acceptable polymer, together with chitosan.

12. The pharmaceutical composition in a solid form of claim 3 characterized in that it is prepared by lyophilizing the composition.

13. The method of claim 4 characterized in that the pH of the solution or non-solid composition is adjusted to about 7.5-10.

14. The method of claim 4 characterized in that the pH of the solution or non-solid composition is adjusted to about 8-9.

15. The method of claim 4 characterized in that the non-solid composition is an aqueous gel and contains PVA and PEG polymers as pharmaceutically acceptable polymer, together with chitosan.

16. The method of claim 4 characterized in that the non-solid composition is an aqueous gel.

* * * * *